United States Patent
Richard et al.

(10) Patent No.: US 6,749,839 B2
(45) Date of Patent: Jun. 15, 2004

(54) PHOTOPROTECTIVE COSMETIC COMPOSITIONS CONTAINING AROMATIC AMIDE, SULPHONAMIDE OR CARBAMATE DERIVATIVES OF ACRYLONITRILE AND NOVEL AROMATIC AMIDE, SULPHONAMIDE OR CARBAMATE DERIVATIVES OF ACRYLONITRILE

(75) Inventors: Hervé Richard, Villepinte (FR); Bernadette Luppi, Mitry Mory (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/174,485

(22) Filed: Jun. 19, 2002

(65) Prior Publication Data

US 2003/0031691 A1 Feb. 13, 2003

(30) Foreign Application Priority Data

Jun. 20, 2001 (FR) .............................. 01 08092

(51) Int. Cl.[7] .............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| 4,661,566 A | * | 4/1987 | Pruett et al. | ............... 525/467 |
|---|---|---|---|---|
| 6,090,374 A | | 7/2000 | Habeck et al. | |
| 6,159,455 A | | 12/2000 | Habeck et al. | |
| 6,627,180 B2 | * | 9/2003 | Candau | ............... 424/59 |

FOREIGN PATENT DOCUMENTS

| EP | 0 413 648 A1 | 2/1991 |
|---|---|---|
| EP | 0 911 020 | 4/1999 |
| EP | 1 005 855 A1 | 6/2000 |
| GB | 1115596 | 5/1968 |

OTHER PUBLICATIONS

Hidaka et al., Chem. Abst. Database Accession No. 1994:163337 XP–002198797, No. 8 (1993), pp. 967–972.
Hidaka et al., Chem. Abst. Database Accession No. 1993:538910 XP–002198798, Chem. Abst. vol. 119, No. 13 (1993), Abstract No. 138910, XP–002198794.
Kawashima et al., Chem. Abst. Database Accession No. 1992:116719 XP–002198799 & Chem. Abst. vol. 116, No. 12 (1992), Abstract No. 116719, XP–002198795.
Hidaka et al., Chem. Abst. Database Accession No. 1993:29821 XP–002198800 & Chem. Abst. vol. 118, No. 4 (1993), Abstract No. 29821, XP–002198796.

* cited by examiner

*Primary Examiner*—Shelley A. Dodson
(74) *Attorney, Agent, or Firm*—Nixon & Vanderhye P.C.

(57) ABSTRACT

Cosmetic compositions for topical use for protecting the skin and the hair, containing, in a cosmetically acceptable support, at least one compound of formula (1) or (2)

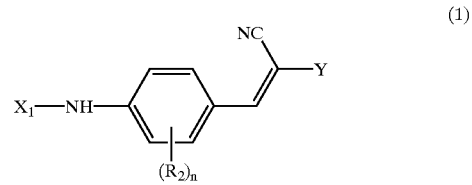

(1)

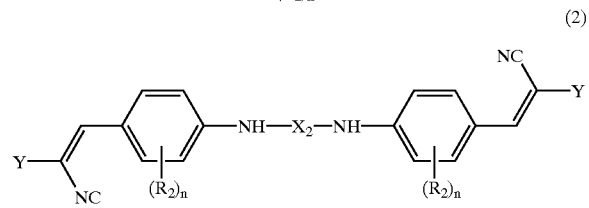

(2)

in which $X_1$ represents $R_3$—(C=O)—, $R_3$—$SO_2$— or $R_3$—O—(C=O)—, $X_2$ represents —(C=O)—$R'_3$—(C=O)—, —$SO_2$—$R'_3$—$SO_2$— or —(C=O)—O—$R'_3$—O—(C=O)—, Y represents —(C=O)—$R_4$ or —$SO_2R_5$, $R_2$ represents a $C_{1-8}$ alkyl group, n is 0, 1 or 2, $R_3$ represents $C_{1-30}$ alkyl or $C_{3-30}$ alkenyl, $R'_3$ represents a single bond or a divalent $C_{1-30}$ alkylene or $C_{3-30}$ alkenylene radical, $R_4$ represents —$OR_6$ or —$NHR_6$, $R_5$ represents $C_{1-30}$ alkyl or a phenyl nucleus, $R_6$ represents $C_{1-30}$ alkyl or $C_{3-30}$ alkenyl, and novel compounds of formula (2).

14 Claims, No Drawings

PHOTOPROTECTIVE COSMETIC COMPOSITIONS CONTAINING AROMATIC AMIDE, SULPHONAMIDE OR CARBAMATE DERIVATIVES OF ACRYLONITRILE AND NOVEL AROMATIC AMIDE, SULPHONAMIDE OR CARBAMATE DERIVATIVES OF ACRYLONITRILE

The present invention relates to cosmetic compositions for topical use, in particular intended for photo-protecting the skin and/or the hair, comprising an effective amount of at least one aromatic amide, sulphonamide or carbamate derivative of acrylonitrile, to novel aromatic amide, sulphonamide or carbamate derivatives of acrylonitrile and to a non-therapeutic process for treating the skin using these compositions.

It is known that radiation with wavelengths of between 280 nm and 400 nm permit tanning of the human epidermis and that radiation with wavelengths of between 280 and 320 nm, known as UV-B radiation, cause skin burns and erythema that may be harmful to the development of a natural tan. For these reasons, and also for aesthetic reasons, there is increasing demand for means for controlling this natural tanning. This UV-B radiation should thus be screened out.

It is also known that UV-A rays, with wavelengths of between 320 and 400 nm, which cause tanning of the skin, are liable to induce adverse changes therein, especially in the case of sensitive skin and/or skin that is continually exposed to solar radiation. In particular, UV-A rays bring about a loss of elasticity of the skin and the appearance of wrinkles, leading to premature ageing of the skin. They promote the onset of the erythemal reaction or amplify this reaction in certain individuals and may even be the cause of phototoxic or photoallergic reactions. Thus, for aesthetic and cosmetic reasons such as maintenance of the natural elasticity of the skin, an increasingly large number of people wish to control the effect of UV-A rays on their skin. It is thus desirable also to screen out UV-A radiation.

UV-A rays are divided into UV-A-1 rays known as "long WV-A" with wavelengths of between 340 and 400 nm, and UV-A-2 rays known as "short UV-A" with wavelengths of between 320 and 340 nm. A good UV-A screening agent should cover these two ranges of wavelengths as much as possible, i.e. it should be a broad UV-A screening agent, without, however, having an intrinsic coloration due to the absorption of light at wavelengths in the visible range. Specifically, an important problem associated with the cosmetic use of coloured screening agents is the staining of fabrics liable to come into contact with these screening agents, such as towels and clothing.

Many compounds intended for protecting the skin against UV-A and/or UV-B radiation have been proposed to date.

Most of these are aromatic compounds that absorb UV radiation in the region between 280 nm and 315 nm, or in the region between 315 nm and 400 nm and above, or alternatively in both these regions. They are usually formulated in antisun compositions that are in the form of oil-in-water emulsions, the lipophilic or hydrophilic organic screening agents being present in dissolved form, in one or other of these phases, in amounts that are suitable to obtain the desired sun protection factor (SPF).

The expression "sun protection factor" means the ratio of the irradiation time required to reach the erythema-forming threshold in the presence of the test screening agent to the irradiation time required to reach this same threshold in the absence of screening agent.

Besides their screening power on solar radiation, photoprotective compounds must also have good cosmetic properties, good resistance to water and perspiration (remanence) and also satisfactory photostability.

Among all the aromatic compounds derived from 2-cyano-acrylic acid that have been proposed for this purpose, mention may be made of the compounds described in patent FR 1 368 808, international patent applications WO 99/36049 and WO 97/15279, and those described in European patent applications EP-A-0 911 020, EP-A-0 716 089 and EP-A-0 005 182. However, none of these screening agents simultaneously satisfies the three conditions of being a broad UV screening agent, that is to say of screening out both long UV-A and short UV-A, and of being uncoloured and photostable.

Mention may also be made of 4-(tert-butyl)-4'-methoxy-dibenzoylmethane, sold under the trade name Parsol® 1789 by the company Hoffman Laroche, which is an uncoloured long UV-A screening agent with a broad spectrum of absorption in the UV-A range, but which has the major drawback of degrading under the effect of solar radiation, that is to say of not being photostable.

The Applicant has discovered, surprisingly, that a particular family of aromatic amide, sulphonamide or carbamate derivatives of acrylonitrile have, simultaneously:

a broad spectrum of UV-A absorption, while at the same time being long UV-A screening agents, an absence of coloration, satisfactory photostability, and good cosmetic properties, and thus constitute excellent sunscreens that may be used, in replacement for Parsol® 1789, in cosmetic compositions, in particular to protect the skin and the hair against the harmful effects of sunlight.

One subject of the present invention is, consequently, a cosmetic composition for topical use, in particular intended for photoprotecting the skin and/or the hair, containing, in a cosmetically acceptable support, at least one compound chosen from the aromatic amide, sulphonamide or carbamate derivatives of acrylonitrile of formula (1) below or the corresponding dimers of formula (2) below.

A subject of the present invention is also the novel compounds of formula (2) below.

Finally, a subject of the present invention is a non-therapeutic process for protecting the skin and/or the hair against solar radiation, which consists in applying to the skin and/or the hair an effective amount of the cosmetic composition defined above.

The aromatic amide, sulphonamide or carbamate derivatives of acrylonitrile used as broad-spectrum UV-A screening agents in the cosmetic compositions of the present invention are compounds corresponding to the general formula (1)

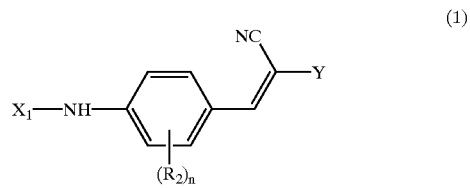

(1)

or dimers of such compounds, corresponding to formula (2):

(2)

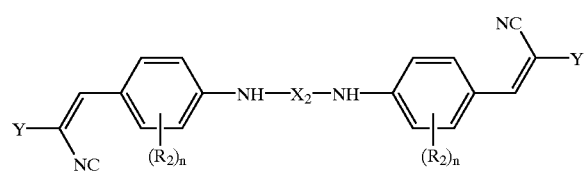

in which $X_1$ represents a radical $R_3$—(C=O)—, $R_3$—$SO_2$— or $R_3$—O—(C=O)—, $X_2$ represents a divalent radical of formula —(C=O)—$R'_3$—(C=O)—, —$SO_2$—$R'_3$—$SO_2$— or —(C=O)—O—$R'_3$—O—(C=O)—, Y represents a radical —(C=O)—$R_4$ or —$SO_2R_5$, $R_2$ represents a linear or branched $C_{1-8}$ alkyl group, n is 0, 1 or 2, $R_3$ represents a linear or branched $C_{1-30}$ alkyl or $C_{3-30}$ alkenyl radical, possibly bearing one or more hydroxyl substituents and possibly containing, in the carbon chain, one or more hetero atoms chosen from oxygen, nitrogen and silicon atoms, $R'_3$ represents a single bond or a linear or branched divalent $C_{1-30}$ alkylene or $C_{3-30}$ alkenylene radical, possibly bearing one or more hydroxyl substituents and possibly containing, in the carbon chain, one or more hetero atoms chosen from oxygen, nitrogen and silicon atoms, $R_4$ represents a radical —$OR_6$ or —$NHR_6$, $R_5$ represents a linear or branched $C_{1-30}$ alkyl radical or a phenyl nucleus that is unsubstituted or substituted with $C_{1-4}$ alkyl or alkoxy radicals, $R_6$ represents a linear or branched $C_{1-30}$ alkyl or $C_{3-30}$ alkenyl radical, possibly bearing one or more hydroxyl substituents and possibly containing, in the carbon chain, one or more hetero atoms chosen from oxygen, nitrogen and silicon atoms.

Although, in formula (1) above, only the isomers in which the cyano substituent is in the cis position relative to the para-aminophenyl substituent have been represented, this formula should be understood as also encompassing the corresponding trans isomer. This is likewise the case for formula (2) in which, for each of the two double bonds, and independently, the cyano and para-aminophenyl substituents may be in a cis or trans configuration relative to each other.

The compounds of formula (2) above are novel compounds.

As mentioned above, the compounds of formulae (1) and (2) have excellent screening power in the broad UV-A range, i.e. in the wavelength range from 320 nm to 400 nm, show satisfactory photostability and are substantially colourless.

Among the compounds of formulae (1) and (2) that are particularly preferred are those in which:

$X_1$ represents a radical $R_3$—(C=O)— or $R_3$—O—(C=O)—, $X_2$ represents a radical —(C=O)—$CH_2$—$CH_2$—(C=O)—, Y represents a radical —(C=O)—$R_4$, n is 0, $R_3$ represents a linear or branched $C_{1-10}$ alkyl radical, $R_4$ represents a radical —O—$R_6$, and $R_6$ represents a linear or branched $C_{1-30}$ alkyl group optionally containing one or more silicon atoms.

The derivatives of formulae (1) and (2) may be prepared according to known methods.

To prepare the derivatives of formula (1), 1 mol of a derivative of formula (3) may be reacted with 1 mol of an acyl chloride, a sulphonyl chloride or a chloroformate of formula (4) in the presence of solvent and of a hydrochloric acid trapping agent, according to the following reaction scheme:

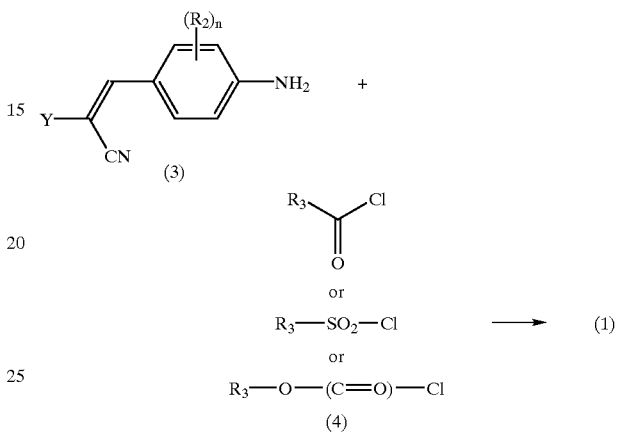

Y, $R_2$, $R_3$ and n having the meanings given above for formula (1). The derivative of formula (3) may be prepared by coupling a compound of formula (5) below with a cyano derivative of formula (6) below according to the reaction scheme:

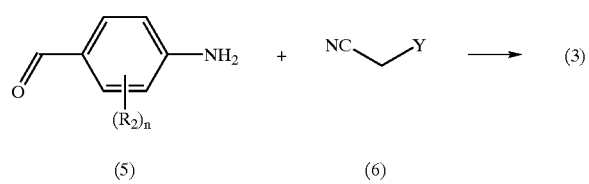

in which $R_2$, Y and n have the meanings given above.

The compound of formula (1) may also be prepared by coupling a compound of formula (7) below with a cyano derivative of formula (6) below according to the following reaction scheme:

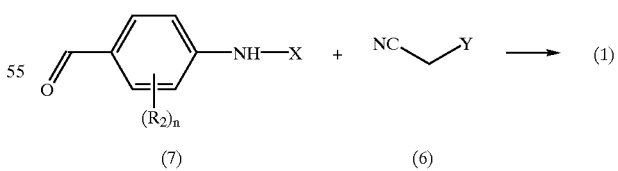

in which Y, $R_2$, X and n have the meanings given above; the derivative (7) may be prepared by coupling a derivative of formula (5) below with an acyl chloride, a sulphonyl chloride or a chloroformate of formula (4) below in the presence of a solvent and of a hydrochloric acid trapping agent, according to the following reaction scheme:

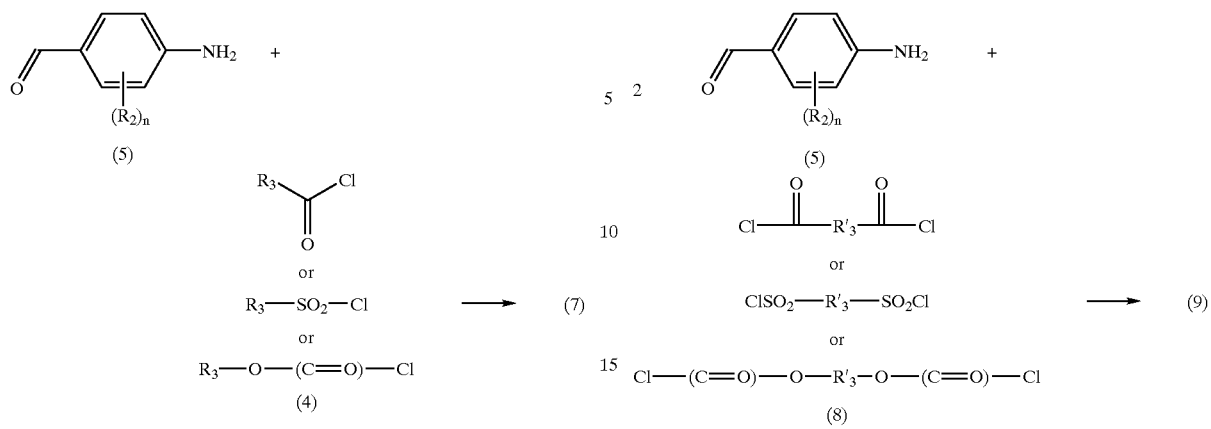

in which $R_2$, $R_3$ and n have the meanings given above.

To prepare the derivatives of formula (2), two moles of a derivative of formula (3), prepared in the manner described above, may be reacted with one mole of a dicarboxylic or disulphonic acid dichloride or a dichloroformate of formula (8) below in the presence of a solvent and of a hydrochloric acid trapping agent, according to the following reaction scheme:

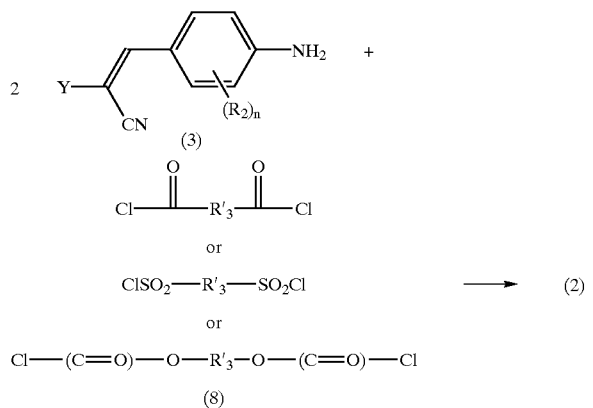

in which Y, $R_2$, $R'_3$ and n have the meanings given above.

The compounds of formula (2) may also be prepared by coupling one mole of a derivative of formula (9) below with two moles of a cyano derivative of formula (6) below:

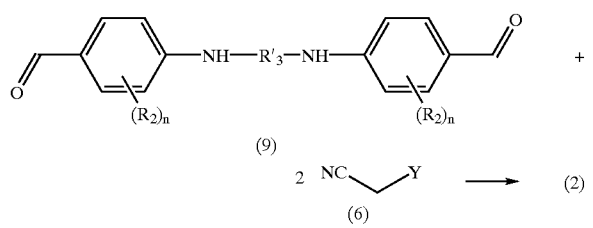

in which Y, $R_2$, $R'_3$ and n have the meanings given above.

The derivative of formula (9) may be prepared by coupling two moles of a derivative of formula (5) below with one mole of a dicarboxylic or disulphonic acid dichloride or a dichloroformate of formula (8) below in the presence of a solvent and of a hydrochloric acid trapping agent, according to the following reaction scheme:

in which $R_2$, $R'_3$ and n have the meanings given above.

The compound(s) of formula (1) or (2) is(are) preferably present in the cosmetic compositions for topical use of the present invention in a proportion of 0.1% and 20% by weight and in particular in a proportion of from 0.5% to 10% by weight, relative to the total weight of the cosmetic composition.

The cosmetic compositions, in particular the antisun compositions, of the present invention can also contain one or more organic sunscreens that are active in the UV-A and/or UV-B range, other than the broad-spectrum UV-A screening agents of formula (1) or (2) described above.

These sunscreens may be chosen especially from cinnamic derivatives, salicylic derivatives, benzylidenecamphor derivatives, triazine derivatives such as those described in the patents or patent applications U.S. Pat. No. 4,367,390, EP 0 863 145, EP 0 517 104, EP 0 570 838, EP 0 796 851, EP 0 775 698, EP 0 878 469, EP 0 933 376 and EP 0 893 119, benzophenone derivatives, β,β'-diphenylacrylate derivatives, phenylbenzimidazole derivatives, anthranilic derivatives, imidazoline derivatives, methylenebis (hydroxyphenylbenzotriazole) derivatives such as those described in the patents or patent applications U.S. Pat. No. 5,237,071, U.S. Pat. No. 5,166,355, GB 2 303 549, DE 19726184 and EP 0 893 119, p-aminobenzoic acid derivatives, and screening hydrocarbon polymers and screening silicones such as those described especially in patent application WO 93/04665.

Examples of such additional UV-A-active and/or UV-B-active sunscreens that may be mentioned include the following compounds, denoted by their NCI name, and also mixtures thereof:

Para-Aminobenzoic Acid Derivatives:
  PABA
  ethyl PABA
  ethyl dihydroxypropyl PABA
  ethylhexyl dimethyl PABA sold especially under the trade name Escalol® 507 by ISP,
  glyceryl PABA,
  PEG-25 PABA sold under the trade name Uvinul® P25 by BASF,
Salicylic Derivatives:
  homosalate sold under the trade name Eusolex® HMS by Rona/EM Industries,
  ethylhexyl salicylate sold under the trade name Neo Heliopan® OS by Haarmann & Reimer,
  dipropylene glycol salicylate sold under the trade name Dipsal® by Scher, TEA salicylate sold under the trade name Neo Heliopan®
TS by Haarmann & Reimer, Cinnamic Derivatives:

ethylhexyl methoxycinnamate sold especially under the trade name Parsol® MCX by Hoffmann Laroche, isopropyl methoxycinnamate isoamyl methoxycinnamate sold under the trade name Neo Heliopan® E 1000 by Haarmann & Reimer, cinoxate, DEA methoxycinnamate, diisopropyl methylcinnamate, glyceryl ethylhexanoate dimethoxycinnamate β,β-Diphenylacrylate Derivatives:

octocrylene sold especially under the trade name Uvinul® 539 by BASF, etocrylene sold especially under the trade name Uvinul® N-35 by BASF, Benzophenone Derivatives:

benzophenone-1 sold under the trade name Uvinul® 400 by BASF, benzophenone-2 sold under the trade name Uvinul® D-50 by BASF, benzophenone-3 or oxybenzone sold under the trade name Uvinul® M-40 by BASF, benzophenone-4 sold under the trade name Uvinul® MS-40 by BASF, benzophenone-5, benzophenone-6 sold under the trade name Helisorb® 11 by Norquay, benzophenone-8 sold under the trade name Spectrasorb® UV-24 by American Cyanamid benzophenone-9 sold under the trade name Uvinul® DS-49 by BASF, benzophenone-12

Benzylidenecamphor Derivatives:

3-benzylidenecamphor manufactured under the name Mexoryl® SD by Chimex, 4-methylbenzylidenecamphor sold especially under the trade name Eusolex® 6300 by Merck, benzylidenecamphorsulphonic acid manufactured under the name Mexoryl® SL by Chimex, camphorbenzalkoniummethosulphate manufactured under the name Mexoryl® SO by Chimex, terephthalylidenedicamphorsulphonic acid manufactured under the name Mexoryl® SX by Chimex, polyacrylamidomethylbenzylidenecamphor manufactured under the name Mexoryl® SW by Chimex, Phenylbenzimidazole Derivatives:

phenylbenzimidazolesulphonic acid sold especially under the trade name Eusolex® 232 by Merck benzimidazilate sold under the trade name Neo Heliopan® AP by Haarmann & Reimer Triazine Derivatives:

anisotriazine sold under the trade name Tinosorb® S by Ciba Geigy, ethylhexyltriazone sold especially under the trade name Uvinul® T150 by BASF, diethylhexylbutamidotriazone sold under the trade name Uvasorb® HEB by Sigma 3V, Phenylbenzotriazole Derivatives:

drometrizole trisiloxane sold under the trade name Silatrizole® by Rhodia Chimie, methylenebis(benzotriazolyl)tetramethylbutylphenol sold in solid form under the trade name Mixxim® BB/100 by Fairmount Chemical or in micronized form as an aqueous dispersion under the trade name Tinosorb® M by Ciba Speciality Chemicals, Anthranilic Derivatives:

menthylanthranilate sold under the trade name Neo Heliopan® MA by Haarmann & Reimer, Imidazoline Derivatives:

ethylhexyl dimethoxybenzylidene dioxoimidazoline propionate

Benzalmalonate Derivatives:

polyorganosiloxane containing benzalmalonate functions, sold under the trade name Parsol® SLX by Hoffmann Laroche The organic UV screening agents that are more particularly preferred are chosen from the following compounds:

ethylhexyl salicylate, ethylhexyl methoxycinnamate, octocrylene, phenylbenzimidazolesulphonic acid, terephthalylidenedicamphorsulphonic acid, benzophenone-3, benzophenone-4, benzophenone-5, 4-methylbenzylidenecamphor, benzimidazilate, anisotriazine, ethylhexyltriazone, diethylhexylbutamidotriazone, methylenebis(benzotriazolyl)tetramethylbutylphenol, drometrizoletrisiloxane, and mixtures thereof.

The cosmetic compositions according to the invention may also contain agents for artificially tanning and/or browning the skin (self-tanning agents) such as dihydroxyacetone (DHA).

The cosmetic compositions according to the invention may also contain one or more mineral pigments and in particular metal oxide nanopigments, that are coated or uncoated, such as, for example, nanopigments of titanium oxide in amorphous or crystallized (rutile and/or anatase) form, of iron oxide, of zinc oxide, of zirconium oxide or of cerium oxide. These nanopigments have a mean particle size of between 5 nm and 100 nm and preferably between 10 nm and 50 nm and are all known UV photoprotective agents.

These nanopigments may be coated with known coating agents such as, for example, alumina and/or aluminium stearate.

Such coated or uncoated nanopigments are described, for example, in patent applications EP-A-0 518 772 and EP-A-0 518 773.

The cosmetic compositions may also contain adjuvants usually used in cosmetics, such as fatty substances, organic solvents, silicones, surfactants, anionic, cationic, nonionic or amphoteric polymers or mixtures thereof, thickeners, antioxidants, opacifiers, stabilizers, antifoams, fragrances, preserving agents, fillers, sequestering agents, propellants, pH regulators and colorants, and mixtures thereof.

They may also contain one or more cosmetic active principles chosen, for example, from softeners, hydroxy acids, vitamins, moisturizers, emollients, free-radical scavengers, substance P antagonists and anti-inflammatories, and mixtures of these compounds.

The fatty substances may consist of an oil or a wax or mixtures thereof, and they also comprise fatty acids, fatty alcohols and fatty acid esters. The oils may be chosen from animal, plant, mineral or synthetic oils and especially from hydrogenated palm oil, hydrogenated castor oil, liquid petroleum jelly, liquid paraffin, purcellin oil, volatile or non-volatile silicone oils, isoparaffins, polyolefins, fluoro oils and perfluoro oils. Similarly, the waxes may be chosen from animal, fossil, plant, mineral and synthetic waxes that are known per se, for instance petroleum jelly, paraffin, lanolin, hydrogenated lanolin and acetylated lanolin.

Among the organic solvents that may be mentioned are lower alcohols and polyols such as ethanol, isopropanol, propylene glycol, glycerol and sorbitol.

The thickeners may be chosen especially from modified or unmodified guar gums and cellulose gums, such as hydroxypropyl guar gum, methylhydroxyethylcellulose, hydroxypropylmethylcellulose or hydroxyethylcellulose.

Needless to say, a person skilled in the art will take care to select this or these optional additional compound(s) and/or the amounts thereof such that the advantageous properties intrinsic to the compounds and compositions according to the invention are not adversely affected by the envisaged addition(s).

The cosmetic compositions for topical use of the invention may be prepared according to techniques that are well known to those skilled in the art, in particular those intended for preparing emulsions of oil-in-water or water-in-oil type.

These compositions may be in particular in the form of a lotion, a thickened lotion, a simple or complex emulsion (O/W, W/O, O/W/O or W/O/W emulsion), such as a cream or a milk, in the form of a gel or cream-gel, or in the form of a powder or a solid tube, and may optionally be packaged as an aerosol and may be in the form of a mousse or a spray.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The cosmetic composition of the invention may be used as a composition for protecting the human epidermis or the hair against ultraviolet rays, as an antisun composition or as a makeup product.

When the cosmetic composition according to the invention is used for protecting the human epidermis against UV rays or as an antisun composition, it may be in the form of a lotion, a suspension or a dispersion in solvents or fatty substances, in the form of a nonionic vesicular dispersion or in the form of an emulsion, preferably oil-in-water type, such as a cream or a milk, or in the form of an ointment, a gel, a cream-gel, a solid tube, an aerosol mousse or a spray.

When the cosmetic composition according to the invention is used for protecting the hair against UV rays, it may be in the form of a shampoo, a lotion, a gel, a rinse-out composition, to be applied before or after shampooing, before or after dyeing or bleaching, or before, during or after permanent-waving or straightening the hair, a styling or treating lotion or gel, a lotion or gel for blow-drying or hairsetting, a permanent-waving, straightening, dyeing or bleaching composition for the hair or a hair lacquer.

When the composition is used as a makeup product for the eyelashes, the eyebrows, the skin or the hair, such as an epidermal treatment cream, a foundation, a tube of lipstick, an eyeshadow, a face powder, a mascara, an eyeliner or a colouring gel, it may be in solid or pasty, anhydrous or aqueous form, for instance an oil-in-water or water-in-oil emulsion, a suspension or a gel.

As a guide, for the antisun formulations in accordance with the invention, which contain a support of oil-in-water emulsion type, the aqueous phase generally represents from 50% to 95% by weight and preferably from 70% to 90% by weight, relative to the total formulation, the oily phase from 5% to 50% by weight and preferably from 10% to 30% by weight, relative to the total formulation, and the (co) emulsifier(s) from 0.5% to 20% by weight and preferably from 2% to 10% by weight, relative to the total formulation.

The examples that follow illustrate the invention

EXAMPLE 1

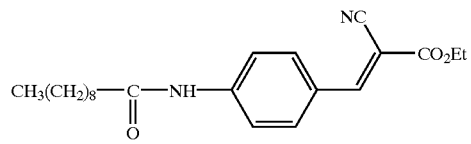

a) Preparation of Ethyl 3-(4-aminophenyl)-2-cyanoacrylate 36 g (0.3 mol) of para-aminobenzaldehyde are suspended in 300 ml of ethanol. 33.9 g (0.3 mol) of ethyl cyanoacetate and a mixture of 0.375 ml of diethylamine and 1.125 ml of acetic acid, as catalyst, are added to the suspension. The reaction mixture is refluxed for 2 hours, left to cool and then crystallized. After separating out the crystals by filtration and drying, 53.9 g (83% yield) of ethyl 3-(4-aminophenyl)-2-cyanoacrylate are obtained in the form of orange-coloured crystals.

b) Preparation of Ethyl 2-cyano-3-(4-decanoylaminophenyl) acrylate 21.6 g (0.1 mol) of the compound synthesized in step a) are dissolved in 300 ml of tetrahydrofuran. 19 g (0.1 mol) of decanoyl chloride are added dropwise at a temperature of 30° C. Gradual thickening of the reaction medium is observed. 10.1 g (0.1 mol) of triethylamine are then added, which is reflected by a temperature increase to 40° C. Stirring is continued for 30 minutes and the reaction mixture is then poured into 500 ml of water. The precipitate obtained is separated out by filtration, washed with water, recrystallized from ethanol and dried. 33.5 g (84% yield) of pale-yellow coloured crystals of ethyl 2-cyano-3-(4-decanoylaminophenyl)acrylate are thus obtained.

Melting point: 76° C.

UV absorption (as a solution in ethanol): $\lambda_{max}$=350 nm, $\epsilon_{max}$=30 380, EI %=820

Elemental analysis for $C_{22}H_{30}N_2O_3$ calculated: C, 71.32; H, 8.16; N, 7.56; O, 12.96. found: C, 71.43; H, 8.26; N, 7.69; O, 13.03.

EXAMPLE 2

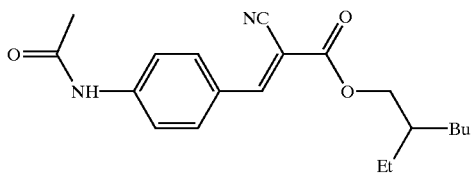

a) Preparation of 2-ethylhexyl 3-(4-acetylaminophenyl)-2-cyanoacrylate

A mixture of 35 g (0.18 mol) of 2-ethylhexyl cyanoacetate and 30 g (0.18 mol) of 4-acetamidobenzaldehyde in 300 ml of isopropanol is refluxed for 3 hours. The reaction mixture is then allowed to cool and is crystallized. The crystals formed are separated out by filtration and are recrystallized from a minimum amount of isopropanol. After filtration and drying, 33.3 g (54% yield) of 2-ethylhexyl 3-(4-acetylaminophenyl)-2-cyanoacrylate are obtained in the form of a pale yellow powder.

Melting point: 119° C.

UV absorption (as a solution in ethanol): $\lambda_{max}$=351 nm, $\epsilon_{max}$=30 960, EI %=904

Elemental analysis for $C_{20}H_{26}N_2O_3$ calculated: C, 70.15; H, 7.65; N, 8.18; O, 14.02. found: C, 70.08; H, 7.65; N, 8.16; O, 14.03.

EXAMPLE 3

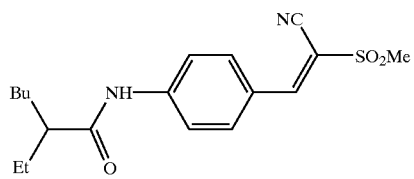

a) Preparation of 3-(4-aminophenyl)-2-methanesulphonyl-acrylonitrile

A mixture of 11.9 g (0.1 mol) of methanesulphonyl-acetonitrile, 12 g (0.1 mol) of 4-aminobenzaldehyde and a catalyst consisting of 0.125 ml of diethylamine and 0.375 ml of acetic acid in 150 ml of ethanol is refluxed for 6 hours. After stopping the reaction, the insoluble materials are removed by hot filtration and the filtrate is concentrated under vacuum, left to cool and crystallized. After filtering off and drying the crystals, 11.6 g (52% yield) of an orange-coloured powder of 3-(4-aminophenyl)-2-methanesulphonylacrylonitrile are obtained.

b) Preparation of 3-[4-(2-ethylhexanoyl)aminophenyl]-2-methanesulphonylacrylonitrile 4 g (0.018 mol) of the compound obtained in step a) are suspended in 50 ml of tetrahydrofuran. 2.9 g (0.018 mol) of 2-ethylhexanoyl chloride are added dropwise at room temperature, which results in a temperature increase to 27° C. The mixture is heated to 45° C. and 1.8 g (0.018 mol) of triethylamine are then added. The resulting mixture is reacted for 1 hour at 60° C. 150 ml of water are then added and the mixture is left to crystallize. The precipitate is separated out by filtration, washed with water and suction-filtered. The product is recrystallized from an isopropanol/water mixture. 3.9 g (62% yield) of a pale yellow powder of the desired compound are thus obtained.

Melting point: 178° C.

UV absorption (as a solution in ethanol): $\lambda_{max}$=348 nm, $\epsilon_{max}$=33 500, EI %=960

Elemental analysis for $C_{18}H_{24}N_2O_3S$ calculated: C, 62.04; H, 6.94; N, 8.04; O, 13.77; S, 9.20. found: C, 61.90; H, 6.88; N, 8.05; O, 13.77; S, 9.13.

EXAMPLE 4

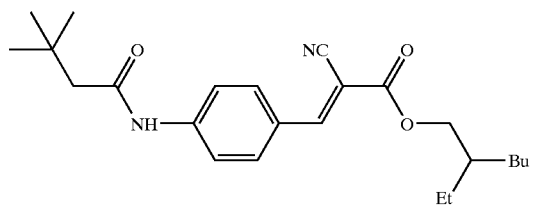

a) Preparation of 2-ethylhexyl 3-(4-aminophenyl)-2-cyanoacrylate 36.3 g (0.3 mol) of p-aminobenzaldehyde are suspended in 450 ml of isopropanol. A mixture of 59.1 g (0.3 mol) of 2-ethylhexyl cyanoacetate and of catalyst (0.375 ml of diethylamine and 1.125 ml of acetic acid) is introduced therein. The mixture is refluxed for 5 hours. The same amount of catalyst is added again and refluxing is continued for a further 4 hours. The insoluble materials are removed by hot filtration and the mixture is concentrated to a volume of 300 ml and left to crystalize. After filtration and drying, 59.6 g (66% yield) of an orange-coloured powder are obtained, and are used without further purification for the following step.

b) Preparation of 2-ethylhexyl 2-cyano-3-[4-(3,3-di-methyl)butyrylamino)phenyl]acrylate 10 g (0.033 mol) of 2-ethylhexyl 3-(4-aminophenyl)-2-cyanoacrylate are dissolved in 50 ml of tetrahydro-furan. 4.48 g (0.033 mol) of tert-butylacetyl chloride are added dropwise at room temperature, resulting in a temperature increase to 29° C. The mixture is heated to about 45° C. and 3.3 g (0.033 mol) of triethylamine are then added. The resulting mixture is heated at 50° C. for 30 minutes. After cooling to room temperature, 150 ml of water are added and the resulting mixture is extracted with dichloromethane. The organic phase is washed with water, dried and concentrated under vacuum. After recrystallizing the solid obtained from heptane, 10.6 g (81% yield) of a pale yellow powder of the desired compound are obtained.

Melting point: 114° C.

UV absorption (as a solution in ethanol): $\lambda_{max}$=355 nm, $\epsilon_{max}$=31 900, EI %=800

Elemental analysis for $C_{24}H_{34}N_2O_3$ calculated: C, 72.33; H, 8.60; N, 7.03; O, 12.04. found: C, 72.40; H, 8.55; N, 7.10; O, 12.28.

EXAMPLE 5

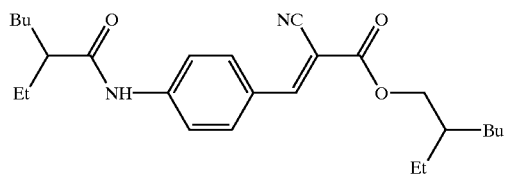

Preparation of 2-ethylhexyl 2-cyano-3-[4-(2-ethyl-hexanoyl)aminophenyl]acrylate 10 g (0.033 mol) of 2-ethylhexyl 3-(4-aminophenyl)-2-cyanoacrylate prepared in accordance with step a) of Example 4 are dissolved in 50 ml of tetrahydrofuran.

5.4 g (0.033 mol) of 2-ethylhexanoyl chloride are added dropwise thereto at room temperature, resulting in a slight temperature increase. The reaction mixture is heated to 45° C. and 3.3 g (0.033 mol) of triethylamine are then added. Heating of the mixture is continued on a water bath for 1 hour 30 minutes. After cooling to room temperature, 150 ml of water are added and the resulting mixture is extracted with dichloromethane and evaporated to dryness. The yellow solid obtained is recrystallized from heptane and 10.8 g (77% yield) of the desired compound are obtained in the form of a pale yellow powder.

Melting point: 68° C.

UV absorption (as a solution in ethanol): $\lambda_{max}$=353 nm, $\epsilon_{max}$=34 300, EI %=804

Elemental analysis for $C_{26}H_{38}N_2O_3$ calculated: C, 73.20; H, 8.98; N, 6.57; O, 11.25. found: C, 73.43; H, 8.86; N, 6.68; O, 11.45.

EXAMPLE 6

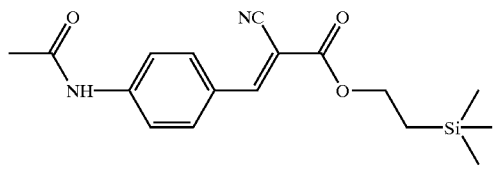

a) Preparation of Ethyl 3-(4-acetylaminophenyl)-2-cyanoacrylate

A mixture of 33.9 g (0.3 mol) of ethyl cyanoacetate and 59.1 g (0.3 mol) of 4-acetamidobenzaldehyde in 300 ml of ethanol in the presence of 5 ml of piperidine is refluxed for 3 hours. The very viscous medium is diluted with 800 ml of hot ethanol. It is filtered while hot. The yellow solid obtained is washed with hot ethanol. After filtration and drying, 32 g (41% yield) of ethyl 3-(4-acetylaminophenyl)-2-cyanoacrylate are obtained in the form of a pale yellow powder.

Melting point: 187° C.

UV absorption (as a solution in ethanol): $\lambda_{max}$=350 nm, $\epsilon_{max}$=31 820, EI %=1 232

Elemental analysis for $C_{14}H_{14}N_2O_3$ calculated: C, 65.11; H, 5.46; N, 10.85; O, 18.58. found: C, 64.89; H, 5.63; N, 11.06; O, 18.38.

b) Preparation of 2-trimethylsilylethyl 3-[4-acetylaminophenyl]-2-cyanoacrylate 2 g (0.0078 mol) of ethyl 3-(4-acetylaminophenyl)-2-cyanoacrylate in 20 ml of 2-trimethylsilylethanol containing 0.1 ml of piperidine are refluxed (150° C.) for 3 hours.

The large excess of 2-trimethylsilylethanol is evaporated off at normal pressure. After cooling to room temperature, 50 ml of heptane are added to the residue. The yellow solid obtained after triturating in heptane is filtered off, washed with heptane and dried. 2.1 g (78% yield) of the desired compound are obtained in the form a pale yellow powder.

Melting point: 136° C.

UV absorption (as a solution in ethanol): $\lambda_{max}$=349 nm, $\epsilon_{max}$=27 450, EI %=830

Elemental analysis for $C_{17}H_{22}N_2O_3Si$ calculated: C, 61.79; H, 6.71; N, 8.48; Si, 8.50. found: C, 61.40; H, 6.80; N, 8.36; Si, 8.15.

EXAMPLE 7

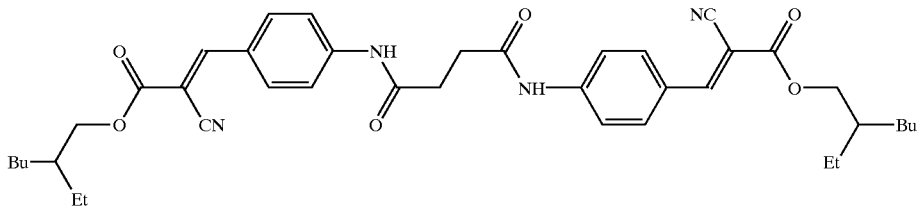

Preparation of the 2-ethylhexyl 2-cyano-3-[4-(acetylaminophenyl]acrylate Dimer 6 g (0.02 mol) of 2-ethylhexyl 3-(4-aminophenyl)-2-cyanoacrylate synthesized in step a) of Example 4 are dissolved in 60 ml of tetrahydrofuran. 1.6 g (0.01 mol) of succinyl chloride are added dropwise at room temperature, resulting in a temperature increase to 36° C. The mixture is heated to about 45° C. and 2.02 g (0.02 mol) of triethylamine are then added. The resulting mixture is heated at 55° C. for 3 hours. The reaction medium, which has become viscous, is cooled to room temperature and filtered. It is washed thoroughly with water, suction-filtered thoroughly and then washed with a minimum amount of 96% ethanol. After drying the solid obtained, 4.6 g (67% yield) of a pale yellow powder of the desired compound are obtained.

Melting point: 235° C.

UV absorption (as a solution in ethanol): $\lambda_{max}$=356 nm, $\epsilon_{max}$=62 620, EI %=917

Elemental analysis for $C_{24}H_{34}N_2O_3$, ½$H_2O$ calculated: C, 69.44; H, 7.43; N, 8.10; O, 15.03. found: C, 69.71; H, 7.39; N, 8.36; O, 15.01.

EXAMPLE 8

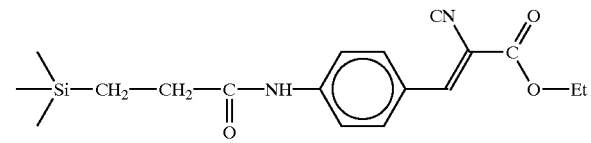

a) Preparation of 3-trimethylsilylpropanoyl Chloride 13.5 g (0.11 mol) of thionyl chloride are added dropwise with stirring to a mixture of 10 g (0.068 mol) of 3-trimethylsilylpropanoic acid in 30 ml of 1,2-dichloroethane. The reaction mixture is heated at 40° C. for 2 hours. The excess thionyl chloride is removed by distillation under reduced pressure. The solution obtained is used without further purification for the following step.

b) Preparation of Ethyl 2-cyano-3-[4-(3-trimethylsilylpropanoylamino)phenyl]acrylate A suspension of 13.7 g (0.0633 mol) of ethyl 3-(4-aminophenyl)-2-cyanoacrylate prepared in accordance with step a) of Example 1 in 80 ml of 1,2-dichloroethane is introduced portionwise at room temperature into the solution obtained above. The heterogeneous reaction mixture is heated to 40° C. and 7.1 g (0.07 mol) of triethylamine are then added dropwise. Heating is continued at between 45 and 50° C. for 1 hour. After cooling to room temperature, the reaction mixture is poured into 500 ml of water. The organic phase is separated out, washed twice with water and dried over sodium sulphate, and the solvent is evaporated off. The solid obtained is recrystallized from 1,2-dichloroethane and 8.5 g (40% yield) of the desired compound are obtained in the form of a pale yellow powder.

Melting point: 157° C.

UV absorption (as a solution in ethanol): $\lambda_{max}$=352 nm, $\epsilon_{max}$=30 730, EI %=892

Elemental analysis for $C_{18}H_{24}N_2O_3Si$ calculated: C, 62.76; H, 7.02; N, 8.13; O, 8.15. found: C, 62.84; H, 7.06; N, 8.16; O, 7.93.

EXAMPLE 9

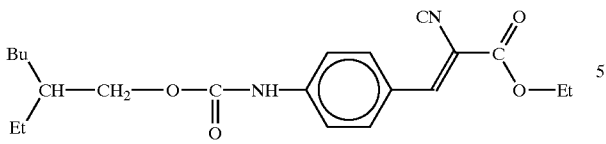

Preparation of Ethyl 2-cyano-3-[4-(2-ethylhexyloxycarbonylamino)phenyl]acrylate 4.3 g (0.02 mol) of ethyl 3-(4-aminophenyl)-2-cyanoacrylate prepared in accordance with step a) of Example 1 are dissolved in 50 ml of tetrahydrofuran.

3.8 g (0.02 mol) of 2-ethylhexyl chloroformate are added dropwise thereto at room temperature, followed by addition of 2.02 g (0.02 mol) of triethylamine. The mixture is heated at 50° C. on a water bath for 2 hours. After cooling to room temperature, 100 ml of water are added, the resulting mixture is extracted with dichloromethane and the extracts are evaporated to dryness. The residue is again extracted with ethyl ether. The paste obtained is chromatographed on silica (eluent: dichloromethane). The fractions containing the desired compound are combined. After evaporation, an oil that crystallizes is obtained. The solid obtained is recrystallized from heptane and 2.2 g (44% yield) of the desired compound are obtained in the form of a pale yellow powder.

Melting point: 105° C.

UV absorption (as a solution in ethanol): $\lambda_{max}$=355 nm, $\epsilon_{max}$=31 860, EI %=856

Elemental analysis for $C_{21}H_{28}N_2O_4$ calculated: C, 67.72; H, 7.58; N, 7.52; O, 17.18. found: C, 67.78; H, 7.45; N, 7.81; O, 17.05.

EXAMPLE 10

| | |
|---|---|
| 2-ethylhexyl 3-(4-acetylaminophenyl)-2-cyanoacrylate (compound of Example 2) | 4 g |
| 80/20 mixture of cetylstearyl alcohol and of oxyethylenated (33 mol of EO) cetyl-stearyl alcohol, sold by the company Tensia under the trade name Dehsconet ® 390 | 7 g |
| mixture of glyceryl monostearate and distearate, sold under the trade name Cerasynth ® SD by the company ISP | 2 g |
| Cetyl alcohol | 1.5 g |
| polydimethylsiloxane sold under the name DC 200 Fluid ® by the company Dow Corning | 1.5 g |
| $C_{12-15}$ alkyl benzoate, sold under the name Finsolv ® TN by the company Finetex | 16 g |
| glycerol | 20% |
| preserving agents | qs |
| demineralized water | qs 100 g |

The sunscreen and the surfactants are dissolved in the fatty phase heated to about 70–80° C. The water heated to the same temperature is then added with vigorous stirring. Stirring is continued for 10 to 15 minutes, the mixture is then allowed to cool with moderate stirring to about 40° C. and the preserving agents are added. An antisun cream that is particularly effective against UV-A and that does not stain the substrates with which it is placed in contact is thus obtained.

What is claimed is:

1. Cosmetic composition for topical use, in particular intended for photoprotecting the skin and/or the hair, containing, in a cosmetically acceptable support, at least one compound of formula (1)

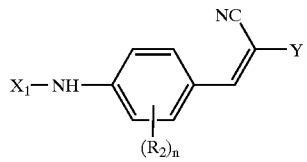

(1)

in which $X_1$ represents a radical $R_3$—(C=O)—, $R_3$—$SO_2$— or $R_3$—O—(C=O)—, Y represents a radical —(C=O)—$R_4$ or —$SO_2R_5$, $R_2$ represents a linear or branched $C_{1-8}$ alkyl group, n is 0, 1 or 2, $R_3$ represents a linear or branched $C_{1-30}$ alkyl or $C_{3-30}$ alkenyl radical, possibly bearing one or more hydroxyl substituents and possibly containing, in the carbon chain, one or more hetero atoms chosen from oxygen, nitrogen and silicon atoms, $R_4$ represents a radical —$OR_6$ or —$NHR_6$, $R_5$ represents a linear or branched $C_{1-30}$ alkyl radical or a phenyl nucleus that is unsubstituted or substituted with $C_{1-4}$ alkyl or alkoxy radicals, $R_6$ represents a linear or branched $C_{1-30}$ alkyl or $C_{3-30}$ alkenyl radical, optionally bearing one or more hydroxyl substituents and further optionally containing, in the carbon chain, one or more hetero atoms chosen from oxygen, nitrogen and silicon atoms.

2. Cosmetic composition according to claim 1, characterized in that $X_1$ represents a radical $R_3$—(C=O)— or $R_3$—O—(C=O)—, Y represents a radical —(C=O)—$R_4$, n is 0, $R_3$ represents a linear or branched $C_{1-10}$ alkyl radical, $R_4$ represents a radical —O—$R_6$, and $R_6$ represents a linear or branched $C_{1-30}$ alkyl radical optionally containing one or more silicon atoms.

3. Cosmetic composition according to claim 1, characterized in that the compound(s) of formula (1) is(are) present in a proportion of from 0.1% to 20% by weight of the cosmetic composition.

4. Cosmetic composition according to claim 1, characterized in that it also contains one or more organic sunscreens that are active in the UV-A and/or UV-B range, other than those of formula (1).

5. Cosmetic composition according to claim 4, characterized in that the organic sunscreens that are active in the UV-A and/or UV-B range, other than those of formulae (1), are chosen from salicylic derivatives, benzylidenecamphor derivatives, triazine derivatives, benzophenone derivatives, cinnamic derivatives, β,β'-diphenylacrylate derivatives, phenylbenzimidazole derivatives, anthranilic derivatives, imidazoline derivatives, methylenebis (hydroxyphenylbenzotriazole) derivatives, p-aminobenzoic acid derivatives, screening hydrocarbon polymers and screening silicones.

6. Cosmetic composition according to claim 5, characterized in that the organic sunscreens that are active in the UV-A and/or UV-B range, other than those of formulae (1), are chosen from the following: ethylhexyl salicylate, ethylhexyl methoxycinnamate, octocrylene, phenylbenzimidazolesulphonic acid, terephthalylidenedicamphorsulphonic acid, benzophenone-3, benzophenone-4, benzophenone-5, 4-methylbenzylidenecamphor, benzimidazilate, anisotriazine, ethylhexyltriazone, diethylhexylbutamidotriazone, methylenebis(benzotriazolyl)tetramethylbutylphenol, drometrizoletrisiloxane, and mixtures thereof.

7. Cosmetic composition according to claim 1, characterized in that it also contains one or more mineral pigments chosen from nanopigments of metal oxides such as titanium oxide, iron oxide, zinc oxide, zirconium oxide and cerium oxide, that are optionally coated, and mixtures thereof.

8. Cosmetic composition according to claim 1, characterized in that it also contains at least one agent for artificially tanning and/or browning the skin.

9. Cosmetic composition according to claim 1, characterized in that it also contains one or more adjuvants chosen from fatty substances, organic solvents, thickeners, antioxidants, opacifiers, stabilizers, antifoams, fragrances, preserving agents, fillers, sequestering agents, propellants, pH regulators, colorants, and cosmetic active principles.

10. Cosmetic composition for protecting the skin against UV rays, according to claim 1, characterized in that it is in the form of a lotion, a suspension, a dispersion, an emulsion, a gel, a cream-gel, an ointment, a solid tube, an aerosol mousse or a spray.

11. Cosmetic composition for protecting the hair against UV rays, according to claim 1, characterized in that it is in the form of a shampoo, a lotion, a gel, a rinse-out composition, a styling or treating lotion or gel, a blow-drying or hairsetting lotion or gel, a permanent-waving, straightening, dyeing or bleaching composition for the hair or a hair lacquer.

12. Cosmetic composition for making up the eyelashes, the eyebrows, the skin or the hair according to claim 1, characterized in that it is in the form of an epidermal treatment cream, a foundation, a tube of lipstick, an eyeshadow, a face powder, a mascara, an eyeliner or a colouring gel.

13. Non-therapeutic process for protecting the skin and/or the hair against solar radiation, characterized in that it consists in applying to the skin and/or the hair an effective amount of a cosmetic composition according to claim 1.

14. Cosmetic composition according to claim 1, characterized in that the compound(s) of formula (1) is(are) present in a proportion of from 0.5% to 10% by weight of the cosmetic composition.

* * * * *